United States Patent
Putaansuu (10) Patent No.: US 10,429,297 B2
(45) Date of Patent: Oct. 1, 2019

(54) MONITORING OPACITY OF SMOKE EXHAUSTED BY WOOD STOVE AND CONTROLLING WOOD STOVE BASED ON SAME

(71) Applicant: Noel Dean Putaansuu, Edmonds, WA (US)

(72) Inventor: Noel Dean Putaansuu, Edmonds, WA (US)

(73) Assignee: Acumentor LLC, Centralia, WA (US)

( * ) Notice: Subject to any disclaimer, the term of this patent is extended or adjusted under 35 U.S.C. 154(b) by 133 days.

(21) Appl. No.: 15/880,033

(22) Filed: Jan. 25, 2018

(65) Prior Publication Data

US 2018/0209903 A1    Jul. 26, 2018

Related U.S. Application Data

(60) Provisional application No. 62/450,794, filed on Jan. 26, 2017.

(51) Int. Cl.
| | | |
|---|---|---|
| G01N 21/53 | (2006.01) | |
| G01K 7/02 | (2006.01) | |
| F24B 1/02 | (2006.01) | |
| G01K 13/00 | (2006.01) | |
| F24B 1/187 | (2006.01) | |
| F24B 1/19 | (2006.01) | |
| F24B 1/189 | (2006.01) | |

(52) U.S. Cl.
CPC .......... *G01N 21/534* (2013.01); *F24B 1/028* (2013.01); *G01K 7/02* (2013.01); *G01K 13/00* (2013.01); *F24B 1/187* (2013.01); *F24B 1/1895* (2013.01); *F24B 1/19* (2013.01); *G01N 2021/536* (2013.01); *G01N 2201/127* (2013.01)

(58) Field of Classification Search
CPC .......... G01N 21/534; G01N 2021/536; G01K 13/00; F24B 1/028; F24B 1/187
See application file for complete search history.

(56) References Cited

U.S. PATENT DOCUMENTS

| | | | | |
|---|---|---|---|---|
| 3,834,326 A | * | 9/1974 | Sowards ................... | F23G 5/30 110/243 |
| 4,309,949 A | * | 1/1982 | Rastogi ..................... | F23N 3/00 110/188 |
| 4,677,426 A | * | 6/1987 | Dattilo ................. | G01N 21/534 250/222.2 |

(Continued)

*Primary Examiner* — David J Laux
(74) *Attorney, Agent, or Firm* — Michael Dryja (57) ABSTRACT

A wood stove monitoring and control device can include a mounting flange mountable to a chimney exhaust pipe of a wood stove. The device can include a ring removably mountable on top of the mounting flange, where the flange is suitably positioned vertically along the exhaust pipe so that the ring is positioned at least partially above an end of the exhaust pipe. The device includes an optical beam source disposed on the ring, and which generates and outputs an optical beam. The device includes an optical sensor positioned on the ring opposite the optical beam source to detect the optical beam output by the optical beam source as the optical beam passes through smoke exhausted by the wood stove through the exhaust pipe. The device can include a temperature probe disposed on the ring to measure a temperature of heat exhausted by the wood stove through the exhaust pipe.

13 Claims, 7 Drawing Sheets

(56) References Cited

U.S. PATENT DOCUMENTS

| | | | | |
|---|---|---|---|---|
| 5,831,730 A * | 11/1998 | Traina | ............... | G01N 15/0205 |
| | | | | 356/336 |
| 5,852,398 A * | 12/1998 | Helman | ............... | F02M 35/09 |
| | | | | 340/438 |
| 6,050,656 A * | 4/2000 | Farahi | ............... | G01N 21/534 |
| | | | | 356/439 |
| 8,070,863 B2 * | 12/2011 | Tsangaris | ............... | C10J 3/00 |
| | | | | 110/216 |
| 8,110,029 B2 * | 2/2012 | Matteson | ............... | B01D 53/34 |
| | | | | 110/216 |
| 8,117,975 B2 * | 2/2012 | Allen | ............... | F23N 5/082 |
| | | | | 110/186 |
| 2018/0062424 A1 * | 3/2018 | Fleischer | ............... | H01L 35/30 |
| 2018/0180280 A1 * | 6/2018 | Neuschaefer | ............... | F23C 5/00 |

\* cited by examiner

MONITORING OPACITY OF SMOKE EXHAUSTED BY WOOD STOVE AND CONTROLLING WOOD STOVE BASED ON SAME

RELATED APPLICATIONS

The present patent application claims priority to the provisional patent application filed on Jan. 26, 2017, and assigned patent application No. 62/450,794, which is hereby incorporated by reference.

BACKGROUND

There are different options that people can choose from to heat their homes. One traditional but still popular way to heat one's home is a wood-burning stove. A wood-burning stove uses an inherently renewable energy source, the wood from trees, which is burned in the stove to generate heat within a home. The smoke that a wood stove generates can be exhausted actively or passively through a chimney.

SUMMARY

An example wood stove monitoring device includes a mounting flange mountable to and fittable over a chimney exhaust pipe of a wood stove. The mounting flange is movably positionable vertically along the chimney exhaust pipe. The monitoring device includes a ring removably mountable on top of the mounting flange. The ring has an interior surface and exterior flat surfaces. The mounting flange is suitably positionable vertically along the chimney exhaust pipe so that the ring is positioned at least partially above an end of the chimney exhaust pipe. The monitoring device includes an optical beam source disposed on a first exterior flat surface of the exterior flat surfaces of the ring. The optical beam source generates and outputs an optical beam perpendicular to the first exterior flat surface and through a corresponding hole within the first exterior flat surface and the interior surface of the ring.

The example wood stove monitoring device includes an optical sensor disposed on a second exterior flat surface of the exterior flat surfaces of the ring opposite to the first exterior flat surface. The optical sensor is linearly aligned with the optical beam source to detect the optical beam output by the optical beam source as the optical beam passes through smoke exhausted by the wood stove through the chimney exhaust pipe. The monitoring device includes a temperature probe disposed on a third exterior flat surface of the exterior flat surfaces of the ring and extending through the third exterior flat surface and the interior surface of the ring. The temperature probe measures a temperature of heat exhausted by the wood stove through the chimney exhaust pipe.

BRIEF DESCRIPTION OF THE DRAWINGS

The drawings referenced herein form a part of the specification. Features shown in the drawing are meant as illustrative of only some embodiments of the invention, and not of all embodiments of the invention, unless otherwise explicitly indicated, and implications to the contrary are otherwise not to be made.

DETAILED DESCRIPTION

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the embodiment of the invention is defined only by the appended claims.

As noted in the background section, houses can be heated using wood-burning stoves. A difficulty with using a wood stove is that if the wood stove is not properly operated and monitored during operation, the wood stove can generate smoke. Many jurisdictions have recognized smoke as a regulated pollutant, to the extent that in certain weather conditions, "no burn days" or "burn bans" are put into effect, limiting the usage of wood-burning stoves.

Furthermore, many jurisdictions have rules in place as to the length of time that a wood-burning stove can generate smoke containing undesired pollutants, such as opaque smoke particles. Such restrictions are generally in the form of smoke minutes. A smoke minute may be defined as a smoke reading that exceeds a threshold opacity, such as 20%, for more than one minute.

A difficulty with using a wood-burning stove is that the operator, who is typically located in the house in which the wood stove is located, has no way of monitoring the opacity of the smoke that the stove is exhausting through a chimney. Therefore, the operator may be satisfied with the wood stove's operation in terms of heat generated, without recognizing that the stove is generating impermissible pollution in the form of smoke. Furthermore, even if a wood stove is not currently generating impermissible pollution, if the operator does not at least periodically tend to the fire within the stove by adding fuel in the form of wood or by controlling the air-fuel mixture by controlling an air intake of the stove, the wood stove can later generate undesired pollution.

Disclosed herein are example wood stove monitoring devices that can monitor the smoke exhausted by a wood stove and that can be used to control operation of the stove. An example stove monitoring device can include an optical beam source to generate and output an optical beam through smoke exhausted by a wood stove via a chimney exhaust pipe. The device can include an optical sensor to detect the optical beam output by the optical beam source as the optical beam passes through the smoke, and processing hardware to correlate the optical beam through the smoke as detected by the optical sensor to an opacity of the smoke exhausted by the wood stove.

The device can include a temperature probe to measure a temperature of heat exhausted by the wood stove through the chimney exhaust pipe. As such, the processing hardware can generate a fresh air intake control signal based on the correlated opacity and the measured temperature. This control signal can control a fresh air intake mechanism of the wood stove to control opacity of the smoke exhausted by the wood stove. The monitoring device can include communication hardware to transmit the signal to the fresh air intake mechanism of the wood stove. The control signal may additionally or alternatively control a thermal oxidizer or other smoke reduction technology mechanism, present at the chimney or at the stove itself, to engage to reduce the opacity of the smoke. Such mechanisms therefore can be controlled based on the generated control signal to regulate the opacity of the exhausted smoke.

In addition to or in lieu of generating the fresh air intake control signal, and transmitting the signal to the fresh air intake mechanism of the wood stove, the wood stove monitoring device can also inform an operator of the stove of the opacity of the smoke that the stove is exhausting. The monitoring device may inform the operator periodically, or just when the opacity of the smoke exceeds a predetermined threshold, such as a threshold corresponding to a percentage of the legally permissible opacity limit. The monitoring device may inform the operator via email, text message, or in another manner, such as via a dedicated smartphone app notification. The operator may be also be informed when the temperature of the exhausted smoke drops below a predetermined threshold temperature, and in this respect may be instructed to add fuel (i.e., wood) to the fire burning in the stove to increase the temperature.

Figure 1:
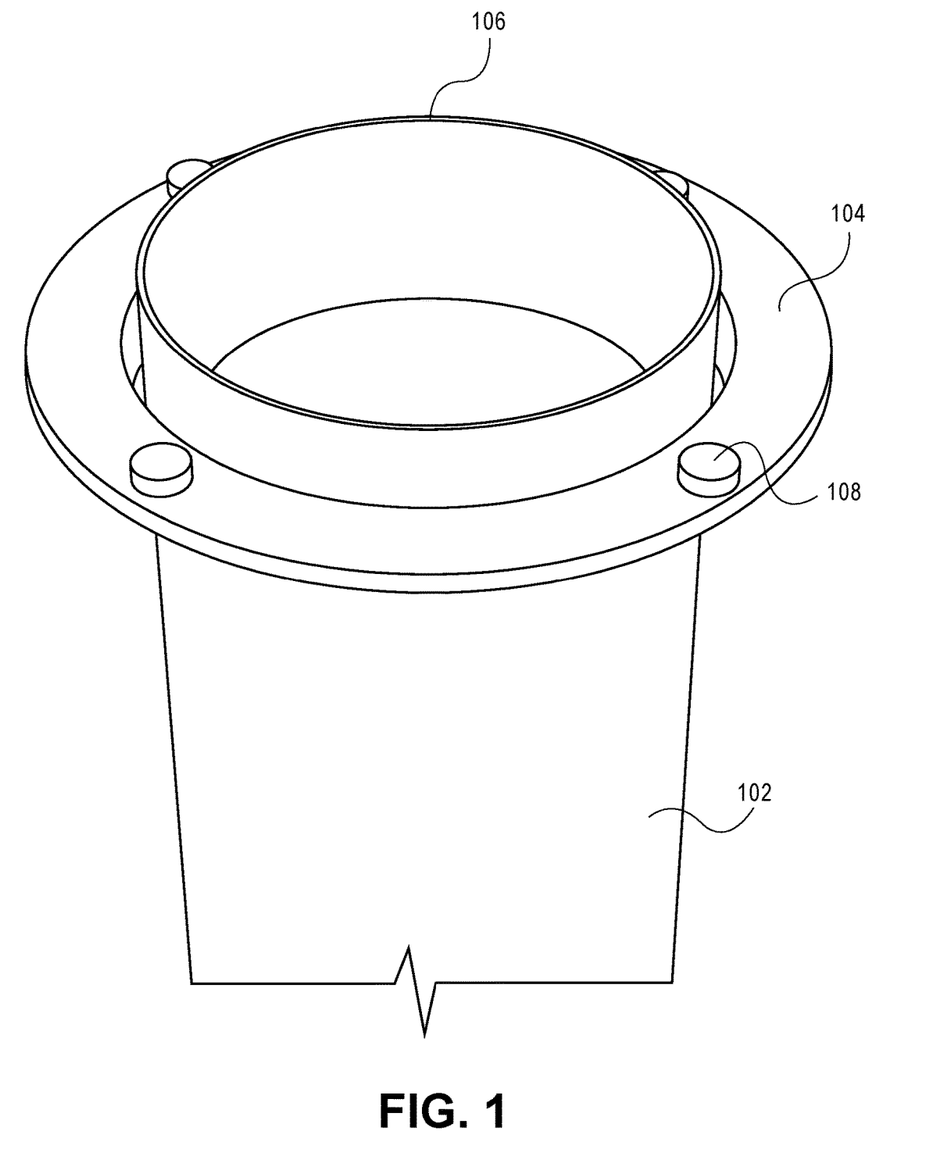
FIG. 1 is a diagram of an example mounting flange of a wood stove monitoring device.

FIG. 1 shows an example mounting flange 104 of a wood stove monitoring device. The mounting flange 104 is mounted to and fitted over a chimney exhaust pipe 102 of a wood-burning stove, where the exhaust pipe 102 has a top end 106. The mounting flange 104 is movably positionable vertically along the pipe 102. For instance, the mounting flange 104 may be fitted over the pipe 102, and then placed at a desired position vertically along the pipe 102, before the flange 104 is then affixed to the pipe 102. The flange 104 may be secured to the pipe 102 via a screw-set clamp, magnets, or in another manner. The example mounting flange 104 can also include multiple magnets 108 on a top surface thereof, uniformly or otherwise disposed along a perimeter of the flange 104.

Figure 2:
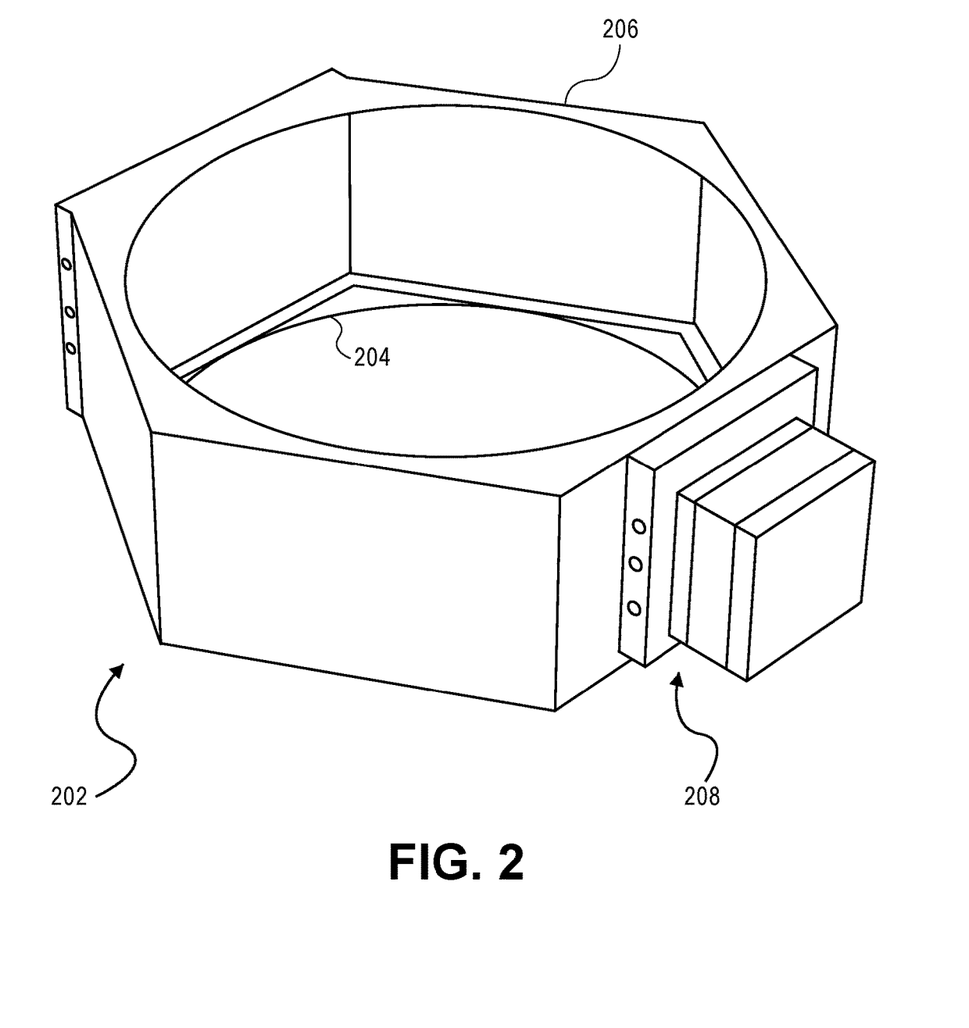
FIG. 2 is a diagram of an example ring of the wood stove monitoring device.

FIG. 2 shows an example ring 202 of a wood stove monitoring device. The ring 202 is removably mountable on top of the mounting flange 104. For instance, the ring 202 may be secure to the flange 104 via the magnets 108 of the flange 104. The mounting flange 104 is suitably positioned vertically along the chimney exhaust pipe 102 so that the ring 202 is at least partially above the top end 106 of the exhaust pipe 102. The ring 202 includes an interior surface 204 that corresponds to the outer shape of the exhaust pipe 102, such as circular or round in FIGS. 1 and 2. The ring 202 also has multiple exterior flat surfaces 206. In the example of FIG. 2, there are six surfaces 206, such that the ring 202 is hexagonal in shape. In other implementations, there may be fewer or more than six surfaces 206, including an implementation in which there are eight surfaces 206, in which case the ring 202 is octagonal in shape. The ring 202 includes a thermal energy generation (TEG) stack 208 disposed on a particular exterior flat surface 206, which generates electrical power from the heat exhausted by the wood stove through its chimney exhaust pipe 102.

Figure 3:
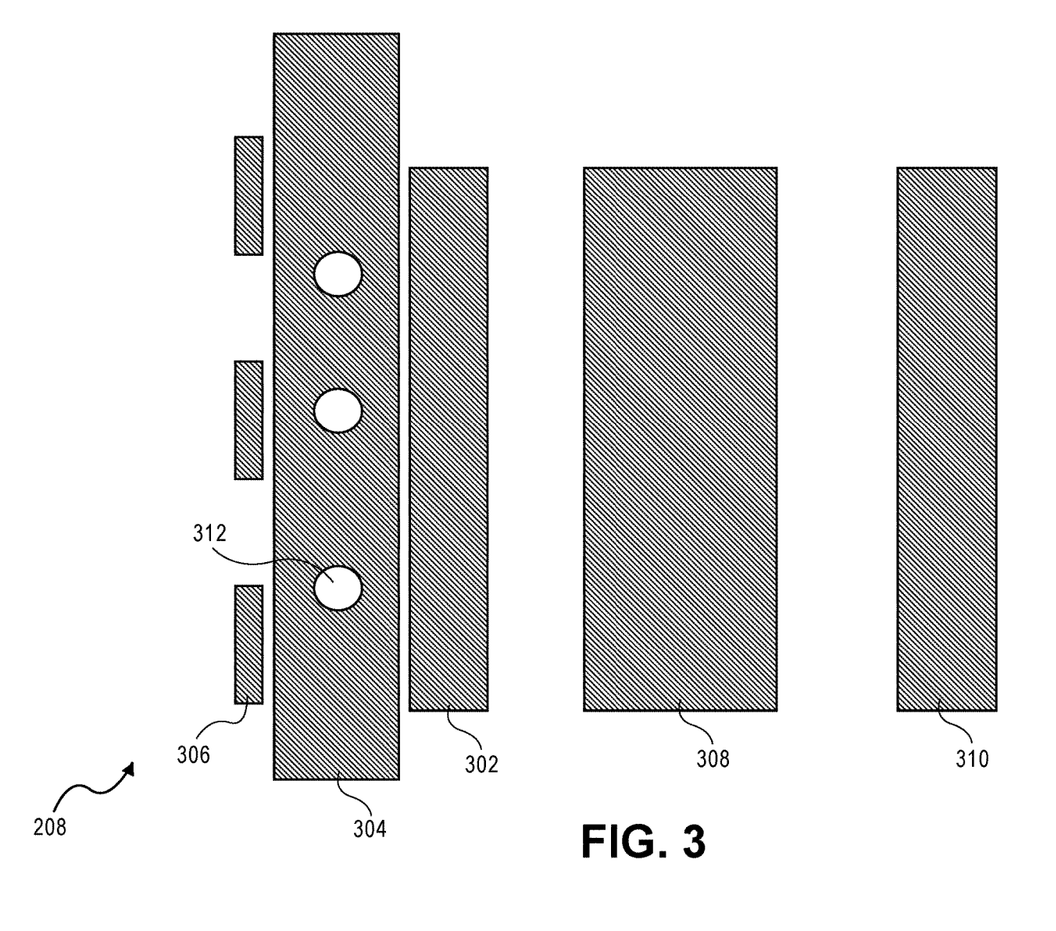
FIG. 3 is a diagram of an example thermal energy generation (TEG) stack of the wood stove monitoring device.

FIG. 3 shows an exploded side profile of an example TEG stack 208 in detail. The TEG stack 208 includes a thermal energy generator 302 that converts the heat exhausted by the wood stove to electrical power. The stack 208 includes a regulating heat transfer plate 304 and shims 306. The shims 306 are adjacent to the particular exterior flat surface 206 of the ring 202, and thus are disposed between the thermal energy generator 302 and the regulating heat transfer plate 304. The regulating heat transfer plate 304 includes cooling channels 312.

As such, heat exhausted by the wood stove is conductively transferred to the thermal energy generator 302 from the ring 202 via the shims 306 and the heat transfer plate 304. The shims 306 and the heat transfer plate 304, the latter via the cooling channels 312, reduce the temperature of the heat conductively transferred to the generator 302 so that the thermal energy generator 302 does not receive excessive thermal energy. The TEG stack 208 also includes a passive heat sink 308 which draws excessive heat from the generator 302, and which is subsequently removed via a fan 310. That is, the passive heat sink 308 draws excessive heat from the generator 302 conductively, and the fan 310 removes the excessive heat via forced convection. The heat sink 308 and the fan 310 can be said to constitute a cooling mechanism of the stack 208.

Figure 4:
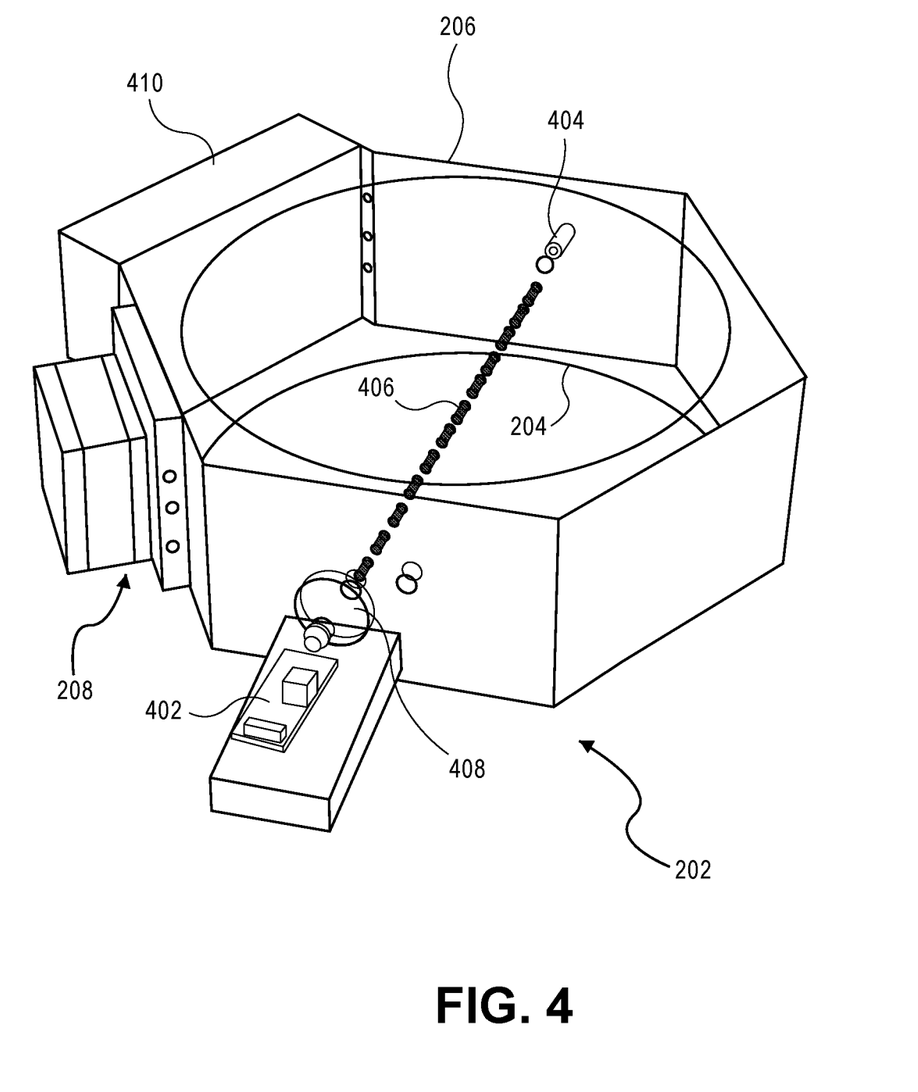
FIG. 4 is a diagram of an example optical beam source, optical sensor, and processing hardware and temperature probe enclosure of the wood stove monitoring device.

FIG. 4 shows an example optical beam source 404 and an optical sensor 402 of a wood stove monitoring device. The optical beam source 404 is disposed at a given exterior surface 206 of the ring 202, and the optical sensor 402 is disposed at an opposite exterior surface 206 of the ring 202. The TEG stack 208 is also depicted in FIG. 4.

The optical beam source 404, such as a laser, generates and outputs an optical beam 406, such as a laser beam, perpendicular to the exterior surface 206 at which the source 404 is mounted, and through a corresponding hole 408 within this exterior surface 206 and the interior surface 204 of the ring. The optical sensor 402 is linearly aligned with the optical beam source 404 to detect the optical beam 406 output by the optical beam source 404 as the beam 406 passes through smoke exhausted by the wood stove through the chimney exhaust pipe 102 of FIG. 1.

A processing hardware enclosure 410 is also depicted in FIG. 4. The enclosure 410 is disposed at another exterior surface 206 of the ring 202, and encloses processing and other hardware that is communicatively connected to the optical beam source 404 and the optical sensor 402. The processing and other hardware within the enclosure 410, as well as the optical beam source 404 and/or the optical sensor 402, can receive power generated by the TEG stack 208, and therefore may be conductively connected to the TEG stack 208.

Figure 5:
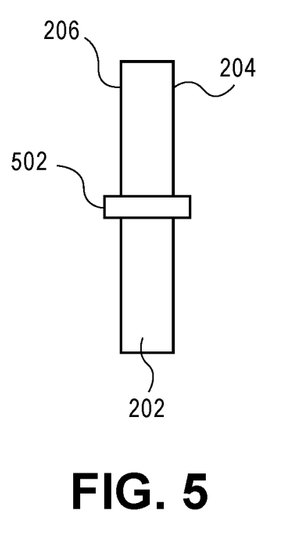
FIG. 5 is a diagram of an example temperature probe of the wood stove monitoring device.

FIG. 5 shows a cross-sectional side view of an example temperature probe 502 of a wood stove monitoring device. The temperature probe 502 is mounted at a specific exterior surface 206 of the ring 202, and extends through this exterior surface 206 and through the interior surface 204 of the ring 202. The temperature probe 502 can thus measure the temperature of heat exhausted by the wood stove through the chimney exhaust pipe of FIG. 1. The temperature probe 502 may also be powered by the power generated by the TEG stack 208. For instance, the temperature probe 502 may be indirectly powered by the power generated by the TEG stack 208. As an example, the TEG stack 208 may power a microcontroller, which is generally described as processing hardware later in the detailed description, and the temperature probe 502 then receiving a set voltage from the microcontroller. In such instance, the temperature probe 502 may be a thermocouple, for instance.

Figure 6:
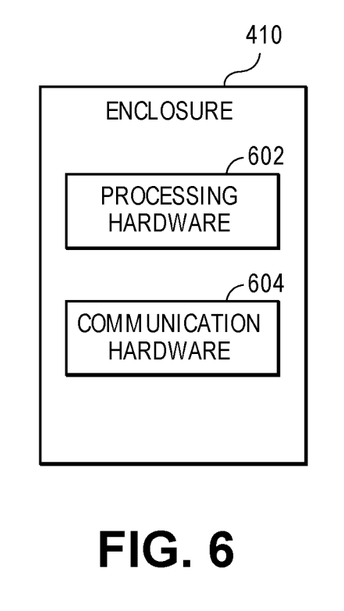
FIG. 6 is a block diagram of an example processing hardware enclosure of the wood stove monitoring device.

FIG. 6 shows a block diagram of an example processing hardware enclosure 410 of a wood stove monitoring device. The enclosure 410 encloses processing hardware 602 and communication hardware 604. The processing hardware 602 can include a processor and a non-transitory computer-readable data storage medium that stores program code executable by the processor, an application-specific integrated circuit (ASIC), or other processing hardware. The communication hardware 604 can include wireless communication hardware, such as Wi-Fi, mobile telephony (e.g., LTE), Bluetooth, or other wireless communication hardware. The hardware 602 and 604 can be powered by the TEG stack 208 of FIG. 2, and therefore may be conductively connected to the stack 208.

The processing hardware 602 can correlate the optical beam 406 as detected by the optical sensor 402 to the opacity of the smoke exhausted by the wood stove through the chimney exhaust pipe 102. The processing hardware 602 may further generate a fresh air intake control signal based on this correlated opacity and the temperature of the smoke exhausted by the wood stove through the chimney exhaust pipe 102 as measured by the temperature probe 502. The processing hardware 602 may control a fresh air intake mechanism of the wood stove, via communicating the control signal to the wood stove using the communication hardware 604, where the control signal may control a damper that adjusts how much fresh air is input into the stove. The control signal is generated to maintain or adjust the smoke exhausted by the wood stove so that the opacity thereof is below a threshold level. The control signal may additionally or alternatively control a thermal oxidizer or other smoke reduction technology mechanism, present at the chimney or at the stove itself, to engage to reduce the opacity of the smoke, as noted above. Furthermore, the processing hardware 602 may also, using the communication hardware 604, notify an operator of the wood stove of the opacity of the smoke being exhausted, such as when the opacity is greater than the threshold level.

Figure 7:
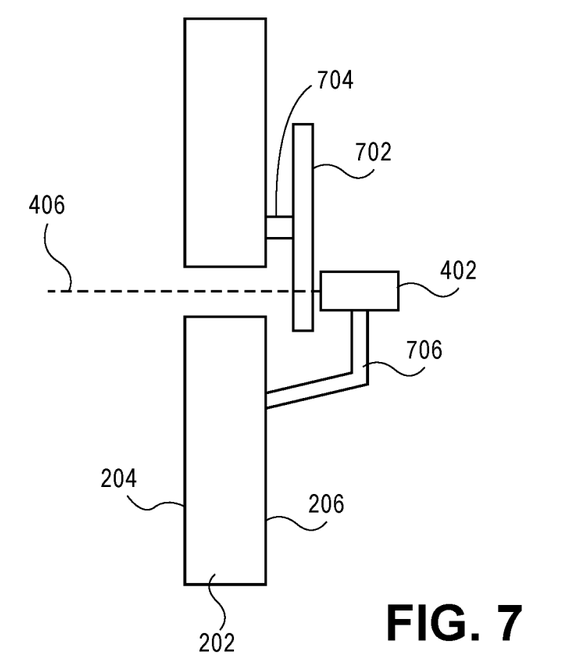
FIG. 7 is a diagram of an example calibration mechanism of a wood stove monitoring device.

FIG. 7 shows a cross-sectional side view of an example calibration mechanism of a wood stove monitoring device. The calibration mechanism can be made up by a calibration wheel 702 and a calibration motor 704. The motor 704 is attached to the exterior surface 206 of the ring 202 to which the optical sensor 402 is attached via, for instance, a mounting arm 706. The calibration wheel 702 is rotatably mounted to the motor 704. Therefore, the motor 704, which may conductively be connected to and be powered by the TEG stack 208 of FIG. 2, can rotate the calibration wheel 702. The wheel 702 is disposed within an optical path of the optical sensor 402, so that a region of the wheel 702 is in optical interference with the sensor 402 receiving the optical beam 406 output by the optical beam source 404 of FIG. 4 through the smoke generated by the wood stove. The region of the wheel 702 that is in current optical interference with the sensor 402 is controlled rotation of the wheel 702 by the motor 704.

Figure 8:
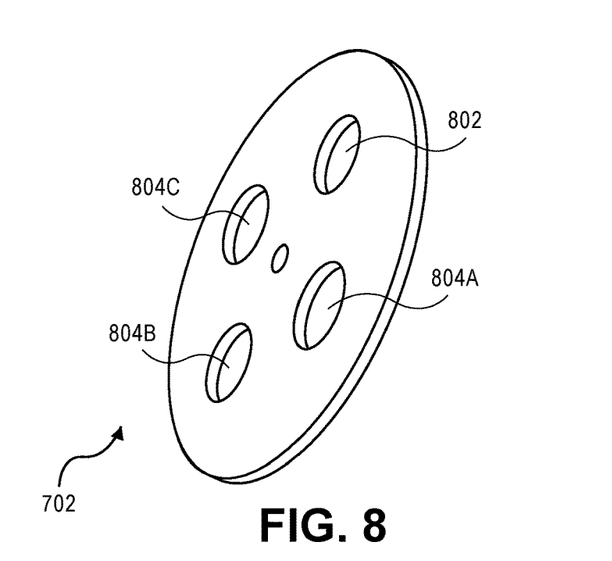
FIG. 8 is a diagram of an example calibration wheel of a calibration mechanism of a wood stove monitoring device.

FIG. 8 shows an example calibration wheel 702 of a calibration mechanism of a wood stove monitoring device. The calibration wheel 702 includes a transparent region 802 and semi-opaque regions 804A, 804B, and 804C, which are collectively referred to as the semi-opaque regions 804. During regular operation of the wood stove monitoring device in which the device is actively being used to detect the opacity of the smoke exhausted by the wood burning stove through the chimney exhaust pipe 102, the motor 704 rotates the wheel 702 so that the transparent region 802 is in optical interference with the optical sensor 402 receiving the optical beam 406.

By comparison, when the wood stove is not in active use, the wood stove monitoring device may be periodically calibrated by the optical sensor 402 detecting the optical beam 406 through the different semi-opaque regions 804. Each region 804 has a different prespecified opacity. The motor 704 rotates the wheel 702 so that a given region 804 is in optical interference with the optical sensor 402 receiving the optical beam 406. The value measured by the optical sensor 402 thus is corresponded to the prespecified opacity of the region 804 in question. This process is repeated for each different semi-opaque region 804. Therefore, the values that the optical sensor 402 outputs can be calibrated so that when wood burning stove is subsequently used, the opacity of the generated smoke is properly determined from the value measured by the optical sensor 402 for the optical beam 406 through the smoke.

Figure 9:
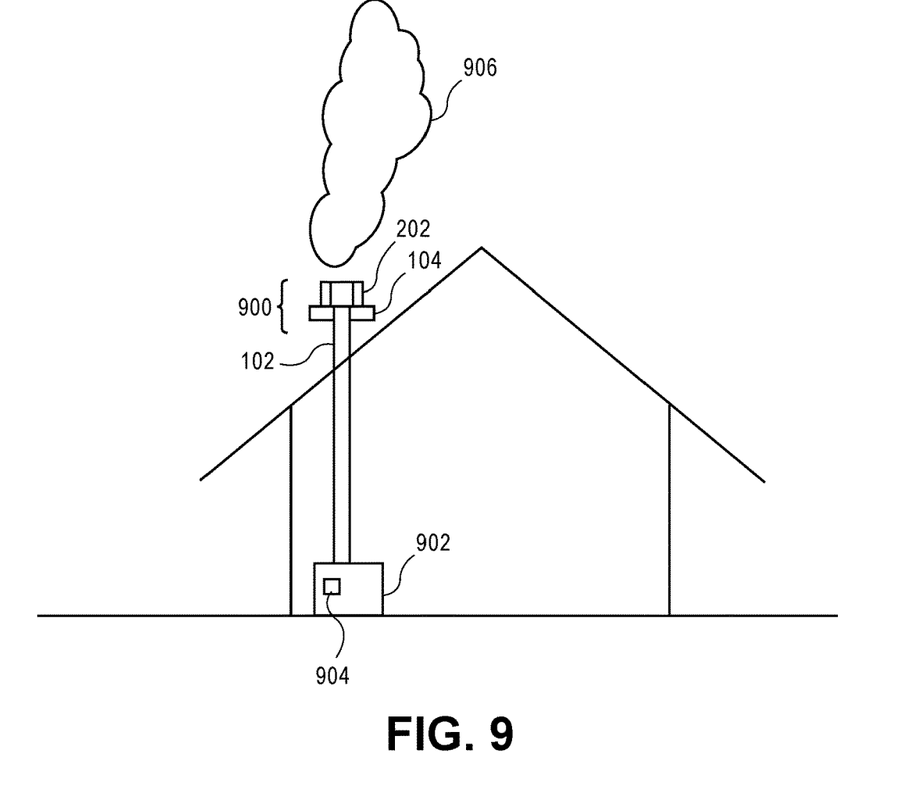
FIG. 9 is a diagram of an example wood stove monitoring device mounted to a chimney exhaust pipe of a wood-burning stove.

FIG. 9 shows an example wood stove monitoring device 900. The wood stove monitoring device 900 includes the mounting flange 104 attached to a chimney exhaust pipe 102 of a wood-burning stove 902, and the ring 202 attached to the mounting flange 104. The wood stove monitoring device 900 can include the other components that have been described. The mounting flange 104 is positioned vertically along the chimney exhaust pipe 102 in FIG. 9 so that the ring 202 is positioned at least partially above the end of the pipe 102. The wood stove monitoring device 900 can wirelessly communicate with a fresh air intake mechanism 904 of the wood-burning stove 902 to control the opacity of smoke 906 generated by the stove 902 and exhausted through the pipe 102.

Figure 10:
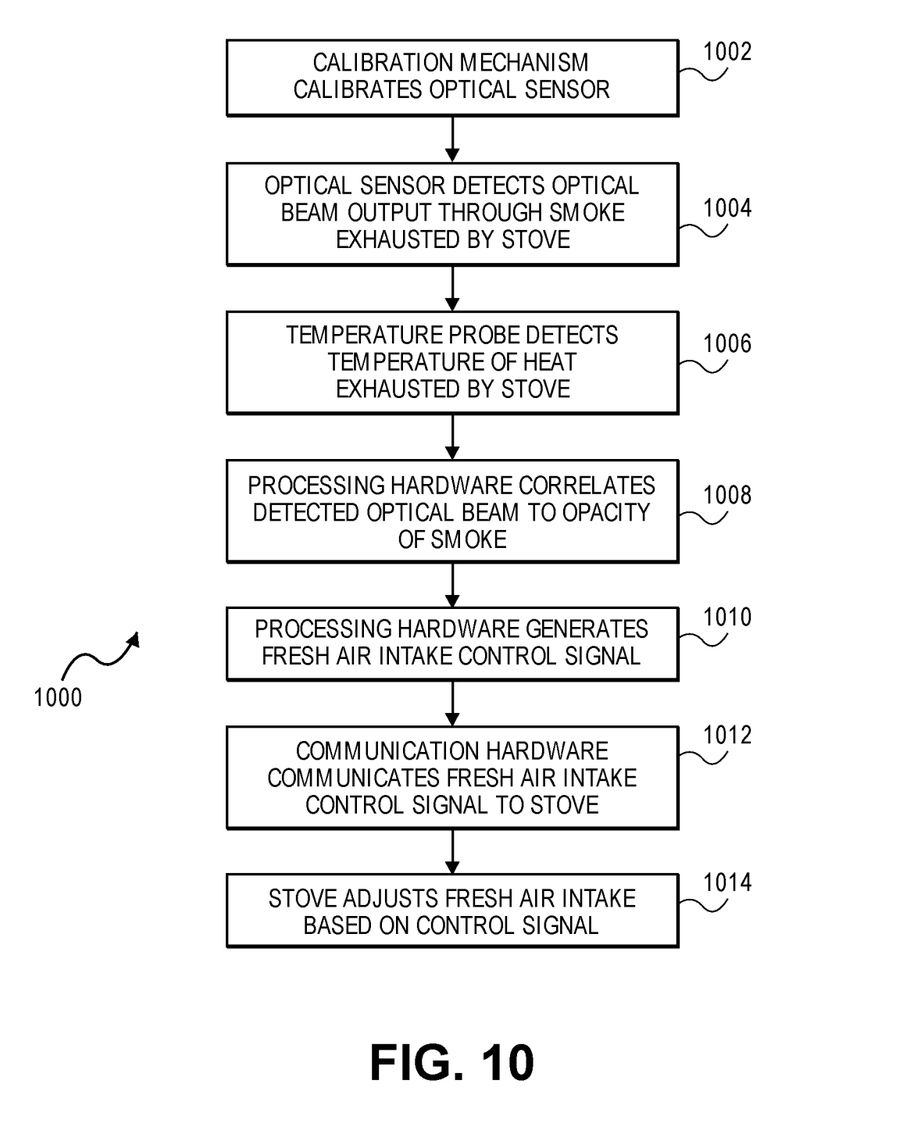
FIG. 10 is a flowchart of an example method for controlling a wood-burning stove using a wood stove monitoring device.

FIG. 10 shows an example method 1000 that can be performed via the wood stove monitoring device 900 to control the wood-burning stove 902 so that the stove 902 outputs smoke with opacity less than a threshold amount. The calibration mechanism of the wood stove monitoring device 900 can first calibrate the optical sensor 402 of the monitoring device 900 (1002). For instance, the motor 704 can rotate the calibration wheel 702 through its various semi-opaque regions 804 while the optical sensor 402 detects the optical beam 406 output by the optical beam source 404, on which basis the optical sensor 402 is then calibrated.

When the wood-burning stove 902 is being used, the optical sensor 402 detects the optical beam 406 output through the smoke 906 exhausted by the stove 902 through the pipe 102 (1004). The temperature probe 502 similarly detects the temperature of the heat exhausted by the stove 902 through the pipe 102 (1006). The processing hardware 602 correlates the optical beam 406 as detected by the optical sensor 402 (i.e., the measured value output by the sensor 402) with or to the opacity of the smoke 906 (1008).

The processing hardware 602 can correspondingly generate a fresh air intake control signal based on the correlated opacity and the measured temperature (1010). The fresh air intake control signal is generated to maintain the opacity of the smoke 906 below a threshold level. For instance, the signal may correspond to increasing fresh air input by the fresh air intake mechanism 904 of the stove 902 responsive to the correlated opacity being greater than a threshold for a predetermined length of time in which the measured temperature is greater than a minimum operating temperature of the stove 902. In this respect, increasing fresh air intake just when opacity is greater than the threshold when the measured temperature is greater than a minimum operating temperature ensures that the stove 902 has sufficient time to initially heat up when first being used.

The fresh air intake control signal may further correspond to decreasing fresh air input by the fresh air intake mechanism 904 of the stove 902 responsive to the correlated opacity being less than the threshold for the predetermined length of time in which the measured temperature is greater than a maximum operating temperature of the stove 902. As such, when the opacity of the smoke 906 is sufficiently low, but the temperature of the stove 902 is too high, the fresh air intake can be reduced to decrease the temperature of the stove 902. Decreasing fresh air, however, can ultimately result in increasing opacity of the smoke 906, such that the fresh air intake control signal may later cause fresh air intake to increase as noted above.

The communication hardware 604 of the wood stove monitoring device 900 thus communicates the generated fresh air intake control signal, such as wirelessly, to the stove 902 (1012). The stove 902 can adjust the fresh air intake based on the received control signal (1014). The method 1000 is continually performed starting at part 1004 once the initial calibration of part 1002 has been performed, for each usage session of the stove 902. The wood stove monitoring device 900 may be powered by a battery to perform the initial calibration, and then be powered by the TEG stack 208 once the stove 902 has generated sufficient heat. As noted above, the control signal may additionally or alternatively be used to control a thermal oxidizer or other smoke reduction technology mechanism to reduce the opacity of the smoke. As also noted above, the communication hardware 604 may also notify an operator of the stove of the opacity of the exhausted smoke, either periodically or when the opacity exceeds a threshold.

The wood stove monitoring device 900 can communicate other information to an operator as well. As noted above, the monitoring device 900 can continually monitor the temperature and opacity of the smoke exhausted by the stove 902. In one scenario, after a length of time, such as thirty minutes, the temperature may be dropping steadily, while the opacity of the exhausted smoke is low. The monitoring device 900 can on this basis conclude that the fuel (i.e., wood) within the stove 902 has been depleted. To prevent smoldering and excessive smoking (i.e., increased opacity exhausted smoke), new fuel should be added to the stove 902 before the temperature drops further. Therefore, the monitoring device 900 can send a signal to the stove 902 or its operator to indicate when new fuel is optimally added. If the temperature continues to decrease, the device 900 may otherwise conclude that no new fuel has been added.

The techniques that have been described herein thus provide for a wood stove monitoring device that can monitor the opacity of smoke that a wood-burning stove generates. The wood stove monitoring device can easily be fitted to existing chimney exhaust pipes, and may not require any wires or cabling between the monitoring device and the stove. As such, residential users are able to continue to use their wood-burning stoves while satisfying any regulations on smoke opacity.

It is finally noted that, although specific embodiments have been illustrated and described herein, it will be appreciated by those of ordinary skill in the art that any arrangement calculated to achieve the same purpose may be substituted for the specific embodiments shown. This application is thus intended to cover any adaptations or variations of embodiments of the present invention. It is manifestly intended that this invention be limited only by the claims and equivalents thereof.

I claim:

1. A wood stove monitoring device comprising:
   a mounting flange mountable to and fittable over a chimney exhaust pipe of a wood stove, the mounting flange movably positionable vertically along the chimney exhaust pipe;
   a ring removably mountable on top of the mounting flange, the ring having an interior surface and a plurality of exterior flat surfaces, the mounting flange suitably positionable vertically along the chimney exhaust pipe so that the ring is positioned at least partially above an end of the chimney exhaust pipe;
   an optical beam source disposed on a first exterior flat surface of the exterior flat surfaces of the ring, the optical beam source generating and outputting an optical beam perpendicular to the first exterior flat surface and through a corresponding hole within the first exterior flat surface and the interior surface of the ring;
   an optical sensor disposed on a second exterior flat surface of the exterior flat surfaces of the ring opposite to the first exterior flat surface, the optical sensor linearly aligned with the optical beam source to detect the optical beam output by the optical beam source as the optical beam passes through smoke exhausted by the wood stove through the chimney exhaust pipe; and
   a temperature probe disposed on a third exterior flat surface of the exterior flat surfaces of the ring and extending through the third exterior flat surface and the interior surface of the ring, the temperature probe measuring a temperature of heat exhausted by the wood stove through the chimney exhaust pipe;
   a thermal energy generation stack disposed on a fourth exterior flat surface of the exterior flat surfaces of the ring, the thermal energy generation stack generating electrical power responsive to heat exhausted by the wood stove through the chimney exhaust pipe,
   wherein the optical beam source and the optical sensor are powered by the electrical power that the thermal energy generation stack generates;
   a heat regulating transfer mechanism to conductively transfer heat from the ring and to reduce the heat transferred from the ring;
   a thermal energy generator having a first surface attached to the heat transfer mechanism and converting the heat transferred by the heat regulating transfer mechanism to the power; and
   a cooling mechanism attached to a second surface of the thermal energy generator opposite the first surface, the cooling mechanism cooling the thermal energy generator.

2. The wood stove monitoring device of claim 1, further comprising:
   processing hardware to correlate the optical beam through the smoke as detected by the optical sensor to an opacity of the smoke exhausted by the wood stove through the chimney exhaust pipe.

3. The wood stove monitoring device of claim 2, wherein the processing hardware is further to generate a control signal based on the correlated opacity and the measured temperature,
and wherein the control signal controls a mechanism of the wood stove to maintain the opacity of the smoke exhausted by the wood stove through the chimney exhaust pipe below a threshold level.

4. The wood stove monitoring device of claim 3, wherein the processing hardware is to generate the control signal to increase fresh air input by a fresh air intake mechanism of the wood stove responsive to the correlated opacity being greater than the threshold for a predetermined length of time in which the measured temperature is greater than a minimum operating temperature of the wood stove.

5. The wood stove monitoring device of claim 4, wherein the processing hardware is to generate the fresh air intake control signal to decrease fresh air input by the fresh air intake mechanism of the wood stove responsive to the correlated opacity being less than the threshold and the measured temperature being greater than a maximum operating temperature of the wood stove.

6. The wood stove monitoring device of claim 3, further comprising:
wireless communication hardware to wirelessly transmit the control signal to the mechanism.

7. The wood stove monitoring device of claim 1, further comprising:
a calibration mechanism providing different prespecified opacities to permit calibration of the optical sensor via the optical beam source outputting the optical beam selectively and individually through the different prespecified opacities.

8. The wood stove monitoring device of claim 7, wherein the calibration mechanism comprises:
a calibration wheel rotatably disposed on the ring and having a plurality of regions including a plurality of semi-opaque regions corresponding to the different prespecified opacities and a transparent region, an active region of the calibration wheel being a current region of the semi-opaque region and the transparent region that is in an optical path between the optical beam source and the optical sensor; and
a motor attached to the calibration wheel to rotate the calibration wheel to select one of the semi-opaque regions and the transparent region as the active region,
wherein during calibration of the optical sensor, the motor rotates the calibration wheel so that the active region in the optical path through the optical beam source and the optical sensor proceeds through the semi-opaque regions while the optical beam source outputs the optical beam,
and wherein during operation of the wood stove monitoring device to monitor opacity of the smoke output by the wood stove through the chimney exhaust pipe, the motor rotates the calibration wheel so that the active region in the optical path is the transparent region of the calibration wheel.

9. A method comprising:
detecting, by an optical sensor of a wood stove monitoring device disposed on a chimney exhaust pipe of a wood stove, an optical beam output by an optical beam source of the optical beam source of the wood stove monitoring device opposite to the optical sensor, the optical beam passing through smoke exhausted by the wood stove through the chimney exhaust pipe between being output by the optical beam source and being detected by the optical sensor;
detecting, by a temperature probe of the wood stove monitoring device, a temperature of heat exhausted by the wood stove through the chimney exhaust pipe;
correlating, by processing hardware of the wood stove monitoring device, the optical beam through the smoke as detected by the optical sensor to an opacity of the smoke exhausted by the wood stove through the chimney exhaust pipe; and
generating, by the processing hardware, a control signal based on the correlated opacity and the measured temperature to regulate the opacity of the smoke exhausted by of the wood stove,
wherein the wood stove monitoring device comprises:
a mounting flange mounted to and fitted over the chimney exhaust pipe, the mounting flange movably positionable vertically along the chimney exhaust pipe;
a ring removably mounted on top of the mounting flange, the ring having an interior surface and a plurality of exterior flat surfaces, the mounting flange suitably positionable vertically along the chimney exhaust pipe so that the ring is positioned at least partially above an end of the chimney exhaust pipe,
wherein the optical beam source is disposed on a first exterior flat surface of the exterior flat surfaces of the ring, the optical beam source generating and outputting an optical beam perpendicular to the first exterior flat surface and through the corresponding hole within the first exterior flat surface and the interior surface of the ring,
wherein the optical sensor is disposed on a second exterior flat surface of the exterior flat surfaces of the ring opposite to the first exterior flat surface, the optical sensor linearly aligned with the optical beam source to detect the optical beam output by the optical beam source as the optical beam passes through smoke exhausted by the wood stove through the chimney exhaust pipe,
wherein the temperature probe is disposed on a third exterior flat surface of the exterior flat surfaces of the ring and extending through the third exterior flat surface and the interior surface of the ring, the temperature probe measuring a temperature of heat exhausted by the wood stove through the chimney exhaust pipe;
a thermal energy generation stack disposed on a fourth exterior flat surface of the exterior flat surfaces of the ring, the thermal energy generation stack generating electrical power responsive to heat exhausted by the wood stove through the chimney exhaust pipe,
wherein the optical beam source and the optical sensor are powered by the electrical power that the thermal energy generation stack generates;
a heat regulating transfer mechanism to conductively transfer heat from the ring and to reduce the heat transferred from the ring;
a thermal energy generator having a first surface attached to the heat transfer mechanism and converting the heat transferred by the heat regulating transfer mechanism to the power; and
a cooling mechanism attached to a second surface of the thermal energy generator opposite the first surface, the cooling mechanism cooling the thermal energy generator.

10. The method of claim 9, wherein the processing hardware generates the control signal to maintain the opacity of the smoke exhausted by the wood stove through the chimney exhaust pipe below a threshold level.

11. The method of claim 10, wherein the processing hardware generates the control signal to increase fresh air input by a fresh air intake mechanism of the wood stove responsive to the correlated opacity being greater than the threshold for a predetermined length of time in which the measured temperature is greater than a minimum operating temperature of the wood stove.

12. The method of claim 11, wherein the processing hardware generates the control signal to decrease the fresh air input by the fresh air intake mechanism of the wood stove responsive to the correlated opacity being less than the threshold and the measured temperature being greater than a maximum operating temperature of the wood stove.

13. The method of claim 9, further comprising:
calibrating, via a calibration mechanism having different prespecified opacities, the optical sensor by advancing a current prespecified opacity in an optical path between the optical beam source and the optical sensor through the different prespecified opacities of the calibration mechanism.

\* \* \* \* \*